United States Patent
Von Bahr

[11] Patent Number: 6,027,445
[45] Date of Patent: Feb. 22, 2000

[54] METHOD FOR FLUSHING AND CALIBRATING A SENSOR IN A BODY FLUID ANALYSIS SYSTEM

[75] Inventor: Pontus Von Bahr, Stockholm, Sweden

[73] Assignee: Siemens Elema AB, Solna, Sweden

[21] Appl. No.: 09/106,777

[22] Filed: Jun. 30, 1998

[30] Foreign Application Priority Data

Jul. 17, 1997 [SE] Sweden .................................. 9702739

[51] Int. Cl.[7] .............................. A61B 5/00; G01N 33/48
[52] U.S. Cl. ........................ 600/309; 204/403; 422/68.1; 436/68
[58] Field of Search ............................. 600/309; 204/403, 204/406, 409; 364/497; 422/68.1; 436/47, 52, 68

[56] References Cited

U.S. PATENT DOCUMENTS 4,786,394  11/1988  Enzer et al. .

FOREIGN PATENT DOCUMENTS

WO 96/22730  1/1996  WIPO .

OTHER PUBLICATIONS

"Integrated pO2,pCO2, pH Sensor System For Online Blood Monitoring," Gumbrecht et al., Sensors and Actuators B, 18–19 (1994), pp. 704–708.

*Primary Examiner*—Eric F. Winakur
*Attorney, Agent, or Firm*—Hill & Simpson

[57] ABSTRACT

In a method for flushing and calibrating at least one sensor in a system for body fluid analysis, said system having a first container, connected to the sensor, holding a first flushing liquid, and a second container, connected to the sensor, holding a second flushing liquid, the flushing liquids having different analytic contents, a calibration measurement is performed with one of the flushing liquids before every body fluid analysis determination, with the different flushing liquids being used alternatively according to a predetermined pattern. The pattern is governed by certain criteria or a combination thereof.

8 Claims, 2 Drawing Sheets

METHOD FOR FLUSHING AND CALIBRATING A SENSOR IN A BODY FLUID ANALYSIS SYSTEM

BACKGROUND OF THE INVENTION

1. Field of the Invention

The present invention relates to a method for flushing and calibrating at least one sensor in a system for body fluid analysis.

2. Description of the Prior Art

When a body fluid, such as blood, undergoes extracorporeal analysis by a known system for continuous or semi-continuous analyses with the aid of a venous or arterial catheter, the heart or an external pump pumps blood to a sensor outside the body. After the blood analysis performed by the sensor, blood is forced back to the body by pumping flushing liquid in the opposite direction. When most of the blood has been forced back to the patient, additional flushing liquid flushes the sensor to remove all remaining blood residue. This flushing liquid can either be infused into the patient or collected in a special bag. When this flushing is performed, the flushing liquid, which is then in contact with the sensor, is sometimes used for calibration. The sensor's characteristics nevertheless change over time. Periodic two-point calibration is commonly performed in order to attain acceptable accuracy and a reasonable operating life for the sensor.

An article entitled "Integrated $pO_2$, $PCO_2$, pH sensor system for on-line blood monitoring", Sensors and Actuators B, 18–19 (1994), pp. 704–708, by Gumbrecht et al. describes a blood analysis system prepared for two-point calibration. The blood analysis system has two calibration pumps, a sampling pump, two liquid containers, a collection container and a sensor arrangement. In conventional two-point calibration, as in the use of the aforementioned blood analysis system, two-point calibration is always performed in two calibration determinations using different flushing liquids between two blood analyses.

In the aforementioned blood analysis system, two-point calibration is performed at certain intervals. To ensure that the flushing liquids really have the right analytic content when intervals between calibrations are long, the tubing must be flushed, a process which is time-consuming and requires a fast pumping rate.

Instability and a shortened operating life for the system in continuous or semi-continuous blood analyses are other disadvantages of this calibration method, since frequent two-point calibration greatly increases intervals between blood analysis determinations.

SUMMARY OF THE INVENTION

It is an object of the present invention to provide a method, suitable for use in a known body fluid analysis system, which avoids the above-identified drawbacks of known techniques.

The known system in which the inventive method is employed includes a first container, in fluid communication with the sensor, holding a first flushing liquid and a second container, also in fluid communication with the sensor, holding a second flushing liquid. These flushing liquids have different analytic contents. In the method according to the present invention, every body fluid analysis is preceded by no more than one calibration measurement using one of the flushing liquids. The different flushing liquids are then used alternatively according to a predetermined pattern, a pattern governed by certain criteria or a combination thereof (i.e., governed by at least one predetermined criterion).

One advantage of the method according to the present invention is that the body fluid analysis system's accuracy and reliability can be increased with no need to increase the interval between body fluid analyses.

This is possible when both flushing liquids are used for 5 calibration and these liquids are used alternately, e.g. every other time. The sensor can then undergo two-point calibration in conjunction with every measuring point when the preceding flushing is used as one point and the following flushing is used as the second point. Calibration will then be much better, without any risk of sudden, unexpected changes in performance causing systematic error over a long period of time.

Another advantage of the method according to the invention is 15 that neither of the flushing liquids needs to remain in tubing very long, so they do not lose their specific gas content (analytic content). Turnover of the two flushing liquids can therefore be relatively fast.

In a first embodiment of the invention, the second liquid is used for every $n^{th}$ calibration measurement, n being a whole number and $n \geq 2$. The first calibration liquid can then be used for other calibrations.

Performing every other calibration with the first flushing liquid and every other calibration with the second flushing liquid is particularly advantageous. This would result in maximal turnover of the flushing liquids with minimal time between each body fluid analysis.

In a second embodiment of the invention, the second flushing liquid is automatically used for calibration measurements when certain criteria are met.

According to a third embodiment, the second flushing liquid is used for calibration measurements after manual operation.

In conjunction herewith, it is advantageous, in a body fluid analysis system which additionally has a collection arrangement connected to the sensor, a first pumping unit connected between the first container and the sensor, a second pumping unit connected between the second container and the sensor and a third pumping unit connected between the collection arrangement and the sensor, to employ an embodiment of the method having the following steps (which do not need to be performed in the stated order).

The first pumping unit pumps the first flushing liquid for flushing the sensor, whereupon the sensor performs a calibration measurement of the first flushing liquid. The sensor then performs a body fluid determination. The second pumping unit pumps the second flushing liquid for flushing the sensor, whereupon the sensor performs a calibration measurement of the second flushing liquid.

The method can also include the step of the third pumping unit pumping the flushing liquids to the collection arrangement during the flushing stages.

An additional advantage is achieved if the method also includes the step of using at least one of the pumping units to pump body fluid to the sensor during body fluid analysis measurements.

In conjunction herewith it is advantageous, with a body fluid analysis system which also has a pressure sensor and a bubble detector between each of the pumping units and the sensor, for the method also to include the step of using the pressure sensor and bubble detector to monitor the pressure and presence of bubbles during blood analysis and calibration measurement stages.

DESCRIPTION OF THE PREFERRED EMBODIMENTS

Figure 1:
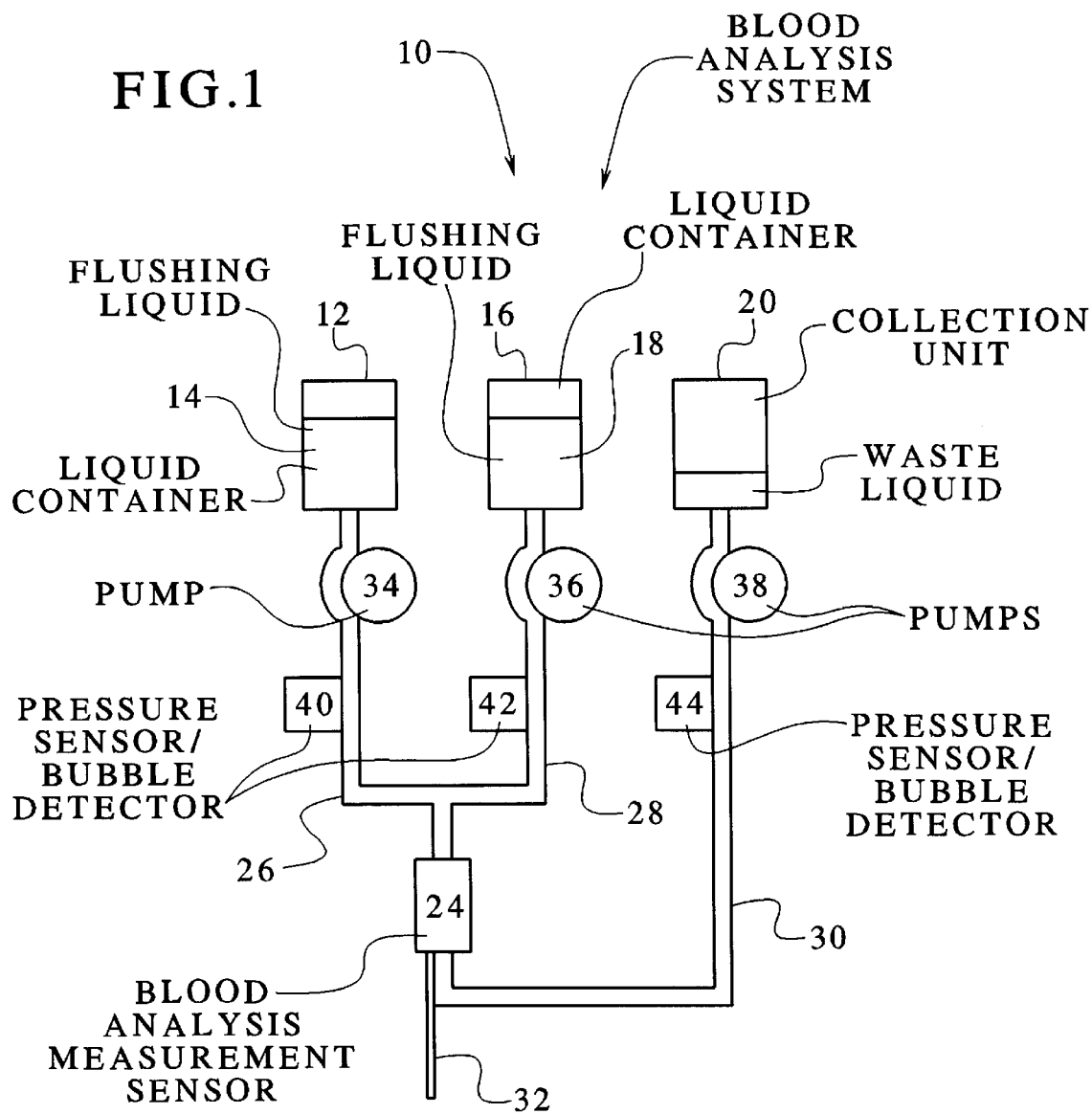
FIG. 1 shows a blood analysis system as one embodiment of a body fluid analysis system operable according to the inventive method.

FIG. 1 shows a blood analysis system 10 for extracorporeal blood analysis as one embodiment of a body fluid analysis system operable according to the inventive method. The blood analysis system 10 has a first container 12 holding a first flushing liquid 14 and a second container 16 holding a second flushing liquid 18. These flushing liquids 14, 18 have different analytic contents. The blood analysis system 10 also includes a collection unit 20 for collecting used flushing liquid, i.e. "waste" liquid 22. The blood analysis system 10 also has a sensor 24 for performing blood analysis measurements. The sensor 24 can e.g. be a chemical sensor. The sensor 24 is connected to the first container 12 by a first tube 26, to the second container 16 by a second tube 28 and to the collection unit 20 by a third tube 30. The sensor 24 is intended for connection, via a fourth tube 32, to a patient's blood circulation by means of a venous or arterial catheter (not shown). The blood analysis system 10 also has a first pumping unit 34 connected between the first container 12 and the sensor 24, a second pumping unit 36 connected between the second container 16 and the sensor 24 and a third pumping unit 38 connected between the collection unit 20 and the sensor 24. All the pumping units 34, 36, 38 are double-acting pumps, i.e. they are capable of pumping in both directions, as schematically designated with the arrows in FIG. 1. The blood analysis system 10 also has a pressure sensor and bubble detector 40, 42, 44, connected between each pumping unit 34, 36, 38 and the sensor 24, which monitors pressure and the presence of bubbles during the blood analysis and calibration stages.

The blood analysis system 10 shown in FIG. 1 is only one example of a known system. This type of blood analysis system 10 can be devised in a number of different ways, e.g. the sensor can be located in different ways.

Figure 2:
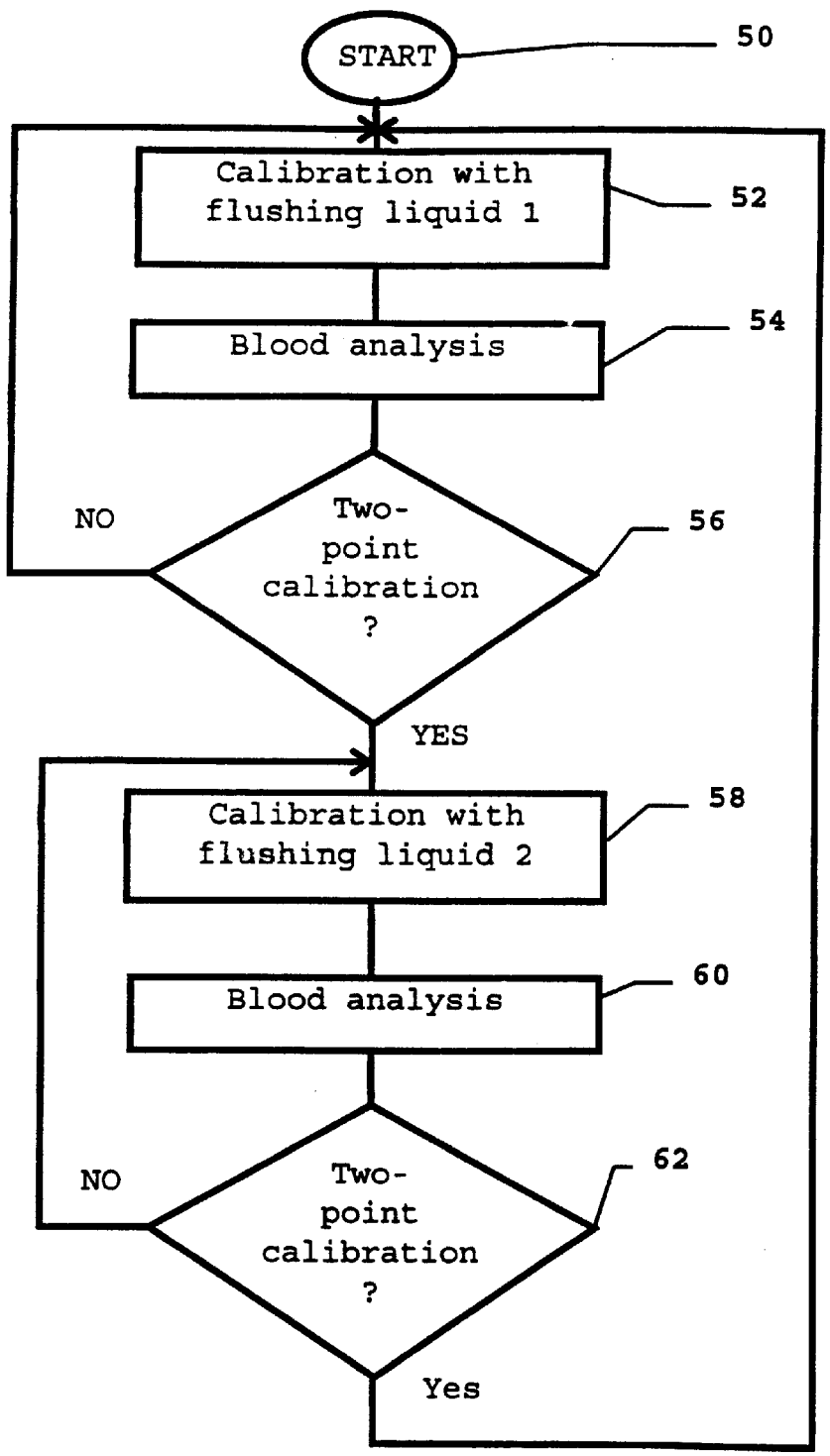
FIG. 2 is a flow chart showing a method according to the invention for flushing and calibrating at least one sensor in the blood analysis system shown in FIG. 1.

FIG. 2 is a flow chart depicting a method according to the invention for flushing and calibrating at least one sensor in a blood analysis system, e.g. a system such as the one described in conjunction with the description of FIG. 1. Even though FIG. 2 shows and the description concerns a method for flushing and calibrating at least one sensor in a blood analysis system, the method is equally applicable to a sensor in a body fluid system. The method starts at block 50. A calibration measurement using one of the flushing liquids, i.e. referred to here as "flushing liquid 1", e.g. the first flushing liquid 14 in FIG. 1, starts at block 52. A blood analysis determination, performed by the sensor 24, then occurs at block 54. Block 56 queries about whether two-point calibration is to be performed. The answer, "yes" or "no", to this query depends, according to the present invention, on the way the various flushing liquids are to be used alternately. According to the method, use is according to a predetermined pattern, a pattern governed by certain criteria or a combination thereof. Blocks 52, 54, 56 are repeated if the reply at query block 56 is "no." But if the reply is "yes" the method continues from block 58, whereupon a calibration measurement is made with flushing liquid 2, i.e. the second flushing liquid 18 in FIG. 1. The sensor 24 then performs a new blood analysis determination at block 60 (cf. FIG. 1) Block 62 queries about whether two-point calibration is to be performed. Whether the reply is "yes" or "no" is determined the same way as in query block 56. If the reply at block 62 is "no", blocks 58, 60 and 62 are repeated. However, if the reply is "yes", the method continues from block 52 etc. The method accordingly continues to be performed in this loop until someone e.g. turns off the blood analysis system 10 or disconnects it from the patient. A pre-defined pattern could be e.g. use of the second flushing liquid 18 for every $n^{th}$ calibration, n being a whole number and $n \geq 2$. It is particularly advantageous for every other calibration to be performed with the first flushing liquid and every other calibration with the second flushing liquid (i.e. n=2). This results in a maximal turnover of the flushing liquids with minimal time between each body fluid analysis.

A pattern governed by certain criteria can entail e.g. automatic use of the second flushing liquid 18 for calibration measurement whenever certain criteria are met. These criteria could be based on e.g. signal drift in the system. Another pattern governed by certain criteria can use the second calibration liquid 18 for manual calibration measurement, i.e. calibration initiated by a physician when needed.

This step, performed at block 52, can be described in greater 30 detail, referring to the system according to FIG. 2, as follows.

The first pumping unit 34 pumps the first flushing liquid 14 to flush the sensor 24. The sensor 24 then performs a calibration measurement of the first flushing liquid 14.

The step performed at block 58 can be described in greater detail as follows.

The second pumping unit 36 pumps the second flushing liquid 18 to flush the sensor 24. The sensor 24 then performs a calibration measurement of the second flushing liquid 18.

The method also can include the step of the third pumping unit 38 pumping used flushing liquid 14, 18 to the collection means 20 during flushing operations.

The method also can include the step of using at least one of the pumping units for pumping blood to the sensor 24 during blood analysis determinations.

The method also can include the step of using a pressure sensor and bubble detector units 40, 42, 44 to monitor pressure and the presence of bubbles during the blood analysis determination and calibration steps. In the above-described method for flushing and calibration, two-point calibration is always executed in such a way that calibration is only performed between two blood analysis determinations. In two-point calibration according to the prior art, two calibration measurements are always performed between every two blood analysis determinations.

With two-point calibration, the output signal's offset (A) and sensitivity (B) can be determined according to $y = A + Bx$. The inventive method is not restricted to the described embodiments. Many variations are possible within the scope of the invention.

A number of variations in the calibration procedure can be employed in the above-described method according to the invention. It is not even necessary for every explicit body fluid analysis to be preceded by a calibration. The choice of sensor, type of body fluid etc. dictate this need. Thus, the method can e.g. be performed so calibration is only carried out before two out of three analyses, two different flushing liquids being utilized for these calibrations. The result is running two—point calibration at three-analysis intervals.

I claim as my invention:

1. A method for flushing and calibrating a sensor in a body fluid analysis system, the system having a first container in fluid communication with the sensor and holding a first flushing liquid, and a second container in fluid communication with the sensor and holding a second flushing liquid, the first and second flushing liquids having respectively different analytic contents, said method comprising the steps of:

(a) conducting a succession of body fluid analyses using said sensor;

(b) preceding each body fluid analysis by no more than one calibration measurement using one of said first and second flushing liquids; and (c) alternatively using said first and second flushing liquids for said calibration measurement according to a predetermined pattern determined by at least one predetermined criterion.

2. A method as claimed in claim 1 wherein the step of alternatively using said first and second flushing liquids comprises using said second flushing liquid for every $n^{th}$ calibration, n being a whole number and $n \geq 2$, and otherwise using said first flushing liquid.

3. A method as claimed in claim 1 wherein the step of alternatively using said first and second flushing liquids comprises automatically using said second flushing liquid for a calibration measurement when said at least one predetermined criterion is present.

4. A method as claimed in claim 1 wherein the step of alternatively using said first and second flushing liquids comprises manually controlling use of said second flushing liquid when said at least one predetermined criterion is present.

5. A method as claimed in claim 1 wherein said body fluid analysis system further includes a collection unit in fluid communication with said sensor for receiving said first and second flushing liquids after usage thereof, a first pump connected between said first container and said sensor, a second pump connected between said second container and said sensor and a third pump connected between said collection unit and said sensor, and wherein steps (a) and (b) comprise:

pumping said first flushing liquid with said first pump to flush said sensor and said sensor performing a calibration measurement of said first flushing liquid, and performing a body fluid analysis using said sensor;

and wherein step (c) comprises:

pumping said second flushing liquid with said second pump to flush said sensor,
      and said sensor performing a calibration measurement of said second flushing liquid.

6. A method as claimed in claim 5 comprising the additional step of pumping the respective first and second flushing liquids with said third pump from said sensor to said collection unit.

7. A method as claimed in claim 6 comprising operating at least one of said first, second or third pumps to pump body fluid to said sensor for conducting said body fluid analysis.

8. A method as claimed in claim 7 comprising the additional steps of:

monitoring pressure and whether bubbles are present at a location between said first pump and said sensor;

monitoring pressure and whether bubbles are present at a second location between said second pump and said sensor; and monitoring pressure and whether bubbles are present at a location between said third pump and said sensor.

* * * * *